United States Patent [19]

White et al.

[11] Patent Number: 4,704,161

[45] Date of Patent: Nov. 3, 1987

[54] PHOTOSYNTHESIS ENHANCEMENT BY SUBSTITUTED α-HYDROXYBUTYNOIC ACIDS AND DERIVATIVES

[75] Inventors: William L. White, Holliston; Karin L. Ricciardelli, Medfield, both of Mass.; Munirathnam K. Chaguturu, Yardley, Pa.

[73] Assignee: The Dow Chemical Company, Midland, Mich.

[21] Appl. No.: 754,481

[22] Filed: Jul. 12, 1985

[51] Int. Cl.[4] .......................................... A01N 37/38
[52] U.S. Cl. ...................................... 71/106; 71/107; 71/108; 71/113; 71/114; 71/115; 71/116
[58] Field of Search ................ 71/106, 113, 107, 108, 71/114, 115, 116

[56] References Cited

U.S. PATENT DOCUMENTS 3,536,762 10/1970 Ashurst et al. ...................... 260/586
4,465,834 8/1984 Bauem et al. ...................... 546/127

FOREIGN PATENT DOCUMENTS 1502349 11/1967 France .
1534145 11/1975 United Kingdom .

OTHER PUBLICATIONS

Hill, R. et al., Bioorg. Chim., 8(2), 175–189, 1979.
Mayrargue, J. et al., Bull. Soc. Chim., Fr(3–4 Pt. 2), 129–132, 1984.
Dugat, D. et al., Bull. Soc. Chim., Fr(12), 4532–4537, 1971.
Synthesis of 3-Unsubstituted 2-Hydroxy-4-Oxoalkanoates, Dec. 1976, Meyer et al., Synthesis, vol. 12, pp. 832–833, (C.A. 86:89130p).
Preparation and Grignard Reactions of 2-Benzoyl-4,-4-Dimethyl-2-Oxazoline, 1976, Hansen and Wang, J. Org. Chem., vol. 41, No. 22, pp. 3635–3637.
Action Des. Organozinciques Acetyleniques sur le Glyoxylate de Butyle, 1962, Golse et al., Bull. Soc. Pharm. Bordeaux, vol. 101, pp. 73–76.
β,γ-Acetylenic α-Hydroxy Nitriles, Synthesis and Transformations in Acidic and Alkaline Media, 1982, Bol'shedvorskaya et al., Zhurnal Org. Khimii, vol. 18, (10), pp. 2053–2056, (C.A. 98:178883b).
Synthesis of Esters of Acetylenic, Secondary α-Hydroxy Acids, 1964, Lapkin et al., Zh. Obshch. Khim., vol. 34(10), pp. 3183–3185, (C.A. 62:3929d).
Synthesis of Esters of Secondary α-Hydroxy Acids of the Acetylene Series, 1966, Lapkin et al., Uch. Zap., Perm. Gos. Univ. No. 159, pp. 285–288.
II. Synthesis of Amino Esters of Acetylenic α-Hydroxy Acids, (1967), Yarovenko et al., Probl. Poluch. Polu-prod. Prom. Org. Sin., Akad., Nauk SSSR, Otd. Obshch. Tekh. Khim., pp. 156–158, (C.A. 68:39427y).
Synthesis of α-Hydroxy-β-Acetylenic Acids and their Oxidation by and Inactivation of Flavoprotein Oxidases, 1974, Cromartie et al., vol. 15, pp. 597–598.
Mechanistic Studies on the Rat Kidney Flavoenzyme L-α-Hydroxy Acid Oxidase, 1975, Biochemistry, vol. 14, No. 15, pp. 3482 to 3490.
Purification and Characterization of Human Liver Glycolate Oxidase, Molecular Weight, Subunit, and Kinetic Properties, 1979, Schwam et al., American Chemical Society, vol. 18, No. 13, 1979, pp. 2826–2833.
Inactivation of a Flavoprotein, Lactate Oxidase, by an Acetylenic Substrate, 1972, The Journal of Biological Chemistry, vol. 247, No. 18, pp. 6004–6006.
Crystallization and Properties of λ-Lactate Oxidase from Mycobacterium smegmatis, 1968, Sullivan, Biochem. J. vol. 110, pp. 363–371.
Toxic Fluorine Compounds, XIX. w-Fluoroalkynes, 1963, Pattison et al., Can. J. of Chem., vol. 41, pp. 2600–2606.
Suicide Enzyme Inactivators, Sep. 1976, Abeles et al., Accounts of Chemical Research, vol. 9, No. 9, pp. 313–319.
Researches on Acetylenic Compounds, Part XXVI, Further Reformatsky Reactions with Propargyl Bromides, 1950, Henbest et al., J. Chem. Soc., pp. 3646–3650.
Transposition Propargylique sur les Halogeno-2 Butyne-3 Oates D'alcoyle, 1967, Verny et al., Bull. de la Soc. Chim. de Fr., pp. 2210–2216.
A Convenient Preparation of Methyl and Ethyl Glyoxylate 1972, Kelly, et al., Synthesis, pp. 544–545.
Inhibition of Glycollate Oxidase from Pea Leaves, May 1975, Jewess et al., Febs Letters, vol. 53, No. 3, pp. 292–296.
n-Butyl Glyoxylate, 1963, Wolf et al., Org. Syn. Coll., vol. 4, pp. 124–125.
Mechanisms of Active Transport in Isolated Bacterial Membrane Vesicles, 1972, Welsh et al., The J. of Biological Chemistry, vol. 247, No. 24, pp. 7858–7863.
Suicide Enzyme Inactivators, 1978, Abeles, Elsevier Biomedical Press, pp. 1–2.

*Primary Examiner*—Paul J. Killos
*Attorney, Agent, or Firm*—Joseph T. Majka; Ronald G. Brookens

[57] ABSTRACT

Novel substituted α-hydroxybutynoic compounds and compositions, are used to increase photosynthesis in plants.

12 Claims, No Drawings

PHOTOSYNTHESIS ENHANCEMENT BY SUBSTITUTED α-HYDROXYBUTYNOIC ACIDS AND DERIVATIVES

FIELD OF THE INVENTION

The present invention relates to novel substituted α-hydroxybutynoic acids and derivatives, their preparation and use as photosynthetic enhancers in plants.

BACKGROUND OF THE INVENTION

Increasing crop yields is probably the single most important objective of any agricultural production program. Several methods are known for increasing crop yield, including the use of fertilizers and pesticides. These methods are limited by the plant's inherent inefficiency in utilizing atmospheric carbon dioxide ($CO_2$) in the biological process known as photosynthesis. In photosynthesis, plants utilize sunlight, carbon dioxide, and water to synthesize carbohydrates such as starch, sugars and celluloses. When water is removed from plants, 90-95 percent (%) of the dry matter remaining is derived from the atmospheric $CO_2$ fixed during photosynthesis. Since crop yield is dependent upon the efficiency of this process, by increasing the efficiency of photosynthesis, crop yield can be similarly increased. At the same time photosynthesis is occurring, another plant process counter-productive to photosynthesis is also operating—photorespiration. Photorespiration, which occurs simultaneously with photosynthesis in plant tissues, is the light-dependent carbon oxidation process by which oxygen ($O_2$) is taken up and $CO_2$ released. Photoerspiration reduces the net $CO_2$ fixing capacity operating in photosynthesis by 20–50 percent (%). Therefore, net photosynthesis (and the subsequent crop yield) can be increased directly by reducing the amount of $CO_2$ lost during photorespiration—a process which has no known function in plant life.

Inhibiting photorespiration will therefore increase net photosynthesis. The present invention has the advantage of providing compounds, compositions and methods for enhancing photosynthesis by inhibiting the first enzyme (glycolate oxidase) of the wasteful photorespiratory pathway. It is believed that inhibiting glycolate oxidase will close down or at least retard photorespiration and thus conserve the carbon which would otherwise be lost as $CO_2$ into the atmosphere. With more carbon available to the plant, the rate of photosynthesis is enhanced, ultimately leading to an increase in crop yield.

SUMMARY OF THE INVENTION

The present invention is directed to novel α-hydroxybutynoic acids, salts and esters thereof having the following formula:

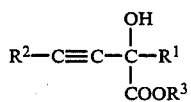

(I)

wherein $R^1$ represents
(a) loweralkyl
(b) hydroxyloweralkyl
(c) substituted cycloalkyl of the formula

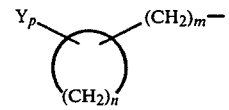

wherein
m is an integer from 0 to 4;
n is an integer from 3 to 6;
Y is hydrogen;
loweralkyl;
loweralkoxy,
halogen,
—$CF_3$,
aryl or
acetal of the formula

wherein
J is loweralkyl and
L is hydrogen,
loweralkyl,
cycloalkyl or
substituted cycloalkyl as defined hereinbefore; and
p is an integer from 0 to the maximum number of positions remaining on the cycloalkyl;
(d) aryl or
(e) substituted aralkyl of the formula

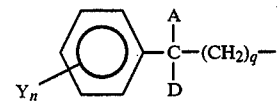

wherein
q is an integer from 0 to 6,
A and D represent hydrogen,
loweralkyl or
lower alkoxy and
Y and n are defined as hereinbefore;
$R^2$ represents $R^1$ or hydrogen; and
$R^3$ represents hydrogen, loweralkyl or counterions of amine, ammonium, sodium, potassium, calcium or magnesium. With the proviso that when $R^3$ is hydrogen, $R^1$ and $R^2$ are not —φ; when $R^3$ is —$C_2H_5$ and $R^2$ is —φ, $R^1$ is not loweralkyl or —φ; and when $R^3$ is —$C_2H_5$ and $R^2$ is —n—$C_5H_{11}$, $R^1$ is not —$CH_3$ or —φ.

The term "plants" is meant to include germinating seed, emerging seedlings and established vegetation.

The terms "active ingredient" or "active material" are defined as the chemical in a formulation primarily responsible for enhancing photosynthesis in the plant or crop.

By "preemergence" is meant the application of the compound to the soil prior to emergence of the specified plant or crop.

By "postemergence" is meant the application of the compound to a specified plant or crop after its emergence.

The term "loweralkyl" is used in the present specification and in the appended claims to designate a straight or branched saturated hydrocarbon moiety (i.e. hydrocarbons having carbon-carbon single bonds) containing from 1 to 6 carbon atoms, such as for example, methyl, ethyl, propyl, isopropyl, butyl, isobutyl, tertbutyl, pentyl, hexyl and the like.

The term "hydroxyloweralkyl" is employed herein to mean a loweralkyl moiety having one or more hydroxyl groups such as for example, hydroxymethyl, dihydroxyethyl and the like.

The term "loweralkoxy" is employed herein to mean a loweralkoxy moiety, such as for example, methoxy, ethoxy, propoxy, isopropoxy, butoxy, pentoxy and the like.

The term "cycloalkyl" is employed herein to mean an alkyl moiety characterized by closed rings and containing from 3 to 6 carbon atoms, such as for example, cyclopropyl, cyclobutyl, cyclopentyl, cyclohexyl, and the like.

The term "aryl" or "Ar" designates an aromatic moiety such as phenyl ($\phi$) and substituted phenyl. Substituted phenyl includes but is not limited to lower alkyl-phenyl such as methylphenyl, dimethylphenyl, trimethylphenyl, ethylphenyl, diethylphenyl, triethylphenyl, methylethylphenyl, dimethylethylphenyl, propylphenyl, butylphenyl, pentylphenyl, hexylphenyl and the like.

The terms "halogen" and "halo" as employed herein, represent fluoride, chloride, bromide and iodide.

In the present specification and claims, the term "sterically compatible" is employed to designate Y, $R^1$ and $R^2$ substituent groups which are not affected by steric hindrance as defined in "The Condensed Chemical Dictionary", 7th Edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or rewarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd Edition, McGraw-Hill Book Co., N.Y. page 215 (1964).

The present invention is also directed to novel compositions useful for increasing photosynthesis in plants, wherein the composition comprises an inert carrier and an amount effective to increase photosynthesis in plants of an $\alpha$-hydroxybutynoic acid, salt or ester of formula I wherein $R^1$, $R^2$ and $R^3$ are as set forth hereinabove, and without the provisos as stated therein.

The present invention is also directed to novel methods for increasing photosynthesis in plants, wherein the method comprises applying to the locus of said plants an amount effective to increase photosynthesis in plants of an $\alpha$-hydroxybutynoic compound of Formula I wherein $R^1$, $R^2$ and $R^3$ are as set forth hereinabove, and without the provisos as stated therein.

Compositions containing an inert carrier and an amount effective to increase photosynthesis in plants of an acitve ingredient of above Formula I wherein $R^1$ is loweralkyl or phenyl constitute a preferred embodiment. More preferably $R^1$ is loweralkyl, and most preferably methyl. The compositions containing an active ingredient where $R^2$ is loweralkyl, phenyl or hydroxyloweralkyl constitute another preferred embodiment of the present invention, more preferably where $R^2$ is loweralkyl or phenyl. In compositions containing active ingredients wherein $R^2$ is loweralkyl, then iso-$C_5H_{11}$ and n-butyl are most preferred. Another preferred class of compositions are those containing active ingredients wherein $R^3$ is hydrogen, loweralkyl or a cation counterion such as amine, sodium, potassium, calcium, magnesium or ammonium. Preferably, $R^3$ is loweralkyl, particularly methyl or ethyl. Most preferably, $R^3$ is hydrogen. Preferred compositions containing active ingredients with the following $R^1$, $R^2$ and $R^3$ designation are presented in descending order of preference:

| $R^1$ | $R^2$ | $R^3$ |
|---|---|---|
| —$CH_3$ | —$\phi$ | —H |
| —$CH_3$ | —$\phi$ | —$CH_3$ |
| —$CH_3$ | —iso-$C_5H_{11}$ | —H |
| —$\phi$ | —$\phi$ | —$CH_3$ |
| —$CH_2H_5$ | —tert-$C_4H_9$ | —H |
| —$CH_3$ | —$CH_2OH$ | —$C_2H_5$ |
| —$C_2H_5$ | —$\phi$ | —H |
| —$CH_3$ | —tert-$C_4H_9$ | —H |

DETAILED DESCRIPTION OF THE EMBODIMENTS

The active ingredients which are esters are generally oils soluble in organic solvents. Active ingredients which are acids are generally crystalline solids or oils soluble in organic solvents. The active ingredients which are salts are generally crystalline solids soluble in water and sparingly soluble in polar solvents such as methanol.

The $\alpha$-hydroxybutynoate esters of Formula I wherein $R^3$ is loweralkyl as defined hereinbefore are readily obtained by the following steps:

(a) reacting the acetylenic Grignard reagent of Formula II with an appropriate $\alpha$-carbonylester of Formula III in the presence of a solvent to form an intermediate magnesium haloalkoxide; followed by (b) hydrolysis of said intermediate with a saturated aqueous ammonium salt solution or a dilute aqueous acid to give the desired $\alpha$-hydroxybutynoate ester of Formula I.

The reaction steps can be schematically illustrated as follows:

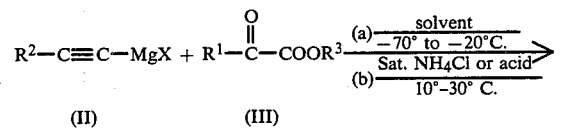

(II)           (III)

(I)

wherein $R^1$ and $R^2$ are as previously defined, $R^3$ is loweralkyl and X is halogen.

In carrying out the reaction for Step (a), equimolar amounts of the acetylenic Grignard reagent and the $\alpha$-carbonyl ester are reacted together in the presence of a suitable solvent such as, for example, diethylether or tetrahydrofuran, using either normal or inverse addition, preferably inverse addition. Where normal addition is employed, the $\alpha$-carbonyl ester is quickly added to the acetylenic Grignard reagent within a period of from about one minute to about 10 minutes at temperatures of from about −70° C. to about −45° C. When inverse addition is employed, the acetylenic Grignard reagent is slowly added to the α-carbonyl ester over a period of from about ½ to about one hour at a temperature between about −10° C. to about −30° C. After all of the above reactants have been combined, the reaction mixture is warmed to room temperature. The reaction is necessarily conducted under anhydrous conditions at ambient pressures and should be agitated or stirred throughout each phase of the reaction.

In carrying out the reaction of Step (b) the intermediate magnesium haloalkoxide from Step (a) is carefully mixed with a saturated solution of an ammonium salt such as aqueous ammonium chloride ($NH_4Cl$), ammonium bromide ($NH_4Br$), ammonium sulfate (($NH_4)_2SO_4$)) and the like, preferably $NH_4Cl$ or with a dilute aqueous acid such as hydrochloric (HCl), sulfuric ($H_2SO_4$) or acetic acid ($CH_3COOH$). Preferably, the ammonium salt or dilute acid is in a concentration of from about 1 to about 5 percent. While the amounts of the reactants are not critical, the reaction generally consumes reactants in the proportion of one mole of the magnesium haloalkoxide reactant to one or more moles of ammonium salt or acid solution. The reaction is usually conducted at temperatures between 10° C. to 30° C., preferably about 20° to 25° C. and is ordinarily carried out under ambient atmospheric pressure.

The resulting reaction mixture from Step (b) is usually maintained, with stirring, for a period of time sufficient to provide completion of the reaction, generally a period of about five minutes to one hour. Typically, the organic phase containing the α-hydroxybutynoate is separated from the aqueous phase. The organic phase is then washed with brine, dried over a drying agent such as magnesium sulfate ($MgSO_4$) and concentrated to dryness under reduced pressure through known recovery procedures. Recovery of the desired product from the crude mixture is achieved by employing conventional separatory and recovery procedures, such as chromatography, distillation, crystallization and the like.

The α-hydroxybutynoic acids of Formula I wherein $R^3$ is hydrogen, (herein defined as $R^{3a}$) are prepared by reacting or saponifying the —$COOR^3$ group in the α-hydroxybutynoate with a slightly excess molar amount of alkali such as sodium carbonate ($Na_2CO_3$) or potassium carbonate ($K_2CO_3$) in a solvent media such as methanol and water. The reaction mixture is heated under a dry inert atmosphere such as nitrogen or helium at temperatures from about 75° C. to about 100° C. After cooling, the aqueous reaction mixture is washed with diethyl ether and is acidified with an aqueous acid such as hydrochloric acid and is extracted with a suitable organic solvent, such as benzene or ether. Impurities may be removed prior to acidification by adding activated carbon such as Darco ® activated carbon (trademark of ICI united States, Inc., Wilmington, Del.) to the aqueous solution and suction filtering the solution through a diatomaceous earth such as Celite ® earth (trademark of Johns-Manville Products Corp., Manville, N.J.). After acidification the organic phase is then washed with brine, dried over a drying agent such as magnesium sulfate ($MgSO_4$) and concentrated to dryness under reduced pressure. The desired α-hydroxybutynoic acid is recovered by conventional separatory and recovery procedures hereinbefore described.

The α-hydroxybutynoic salts of Formula I wherein $R^3$ is an inorganic cation such as $NH_4^+$, $Na^{30}$, $K^{30}$, $Ca^{30}+$, $Mg^{++}$, etc. are conventionally prepared by reacting the α-hydroxybutynoic acid described hereinabove with an appropriate metal alkali of Group IA of the Periodic Table such as sodium hydroxide (NaOH), potassium hydroxide (KOH), sodium carbonate ($Na_2CO_3$), potassium carbonate ($K_2CO_3$) or with an alkaline earth metals of Groups IIA of the Periodic Table such as calcium hydroxide ($Ca(OH)_2$), magnesium hydroxide ($Mg(OH)_2$), calcium carbonate ($CaCO_3$) and the like in a suitable solvent such as water. The ammonium salt ($NH_4^+$) may be prepared by reaction of the α-hydroxybutynoic acid with ammonium hydroxide ($NH_4OH$). The amine salts may be similarly prepared by reacting the α-hydroxybutynoic acids with an appropriate amine, for example, methylamine, diethylamine, triethanolamine, triethylamine, and the like in a suitable solvent such as methanol. A suitable molar ratio of reactants is from about 1:1 to about 1:3 (hydroxybutynoic acid:inorganic cation or amine), preferably in a molar ratio of about 1:1. Generally, the reaction is stirred for about 0.5 hours to about 3 hours or more. The reaction is usually conducted at temperatures from about 20° to about 50° C., preferably about 20°-30° C. and is ordinarily carried out under ambient atmospheric pressure. Recovery of the desired α-hydroxybutynoic salt from the reaction mixture is achieved by employing conventional separatory and recovery procedures described hereinbefore.

Preparation of Starting Materials

Generally, the acetylenic Grignard reagent of Formula II may be prepared by reacting an appropriate monosubstituted acetylenic compound of Formula IV with a preformed Grignard reagent of Formula V in the presence of a suitable solvent to form the acetylenic Grignard reagent. The reaction can be schematically illustrated as follows:

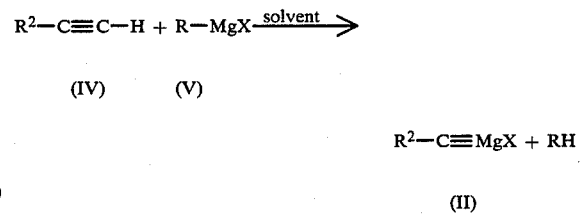

wherein
$R^2$ is as previously defined, R is loweralkyl and X is halogen.

In carrying out this reaction, about one mole of an appropriate monosubstituted acetylenic compound is added to about one mole of the preformed Grignard reagent in the presence of a suitable solvent such as diethylether (ether) or tetrahydrofuran (THF) over a 2 to 3 hour period at temperatures between about 0° C. to about 40° C. The reaction is terminated when the evolution of bubbling alkane gas (RH such as methane, ethane, propane, etc.) ceases, giving the desired acetylenic Grignard reagent. The acetylenic Grignard reagent may be used without further purification.

In the situation where the monosubstituted acetylenic compound contains a carbonyl or a hydroxyloweralkyl

moiety, the carbonyl or the hydroxyloweralkyl must be protected before the monosubstituted acetylenic compound is reacted with the Grignard reagent as described hereinabove.

Protection is provided prior to this reaction, by reacting the carbonyl containing acetylenic compound with a large excess of an acetal such as 2,2-alkoxypropane containing a trace of acid to give the acetylenic dialkyl acetal, which is then reacted with the Grignard reagent to form the acetylenic Grignard reagent.

Hydrolysis or conversion of the dialkyl acetal protecting group back to the desired carbonyl is accomplished by conventional means. Generally, dilute aqueous mineral acid such as hydrochloric acid or acetic acid is added to the isolated α-hydroxybutynoate of Formula I in the presence of a suitable solvent such as tetrahydrofuran and the product purified and recovered by conventional means.

Alternatively, the dialkyl acetal is hydrolyzed to the carbonyl during the simultaneous hydrolysis of the intermediate magnesium haloalkoxide in step (b) described hereinbefore through joint utilization of dilute aqueous acid such as hydrochloric, sulfuric or acetic.

In the situation where the monosubstituted acetylenic compound contains one or more hydroxyl (OH) bearing carbons, the hydroxyl(s) must be protected before the acetylenic compound is reacted with the Grignard reagent as described hereinabove. Protection is provided prior to this reaction by reacting the hydroxyl containing acetylenic compound with an excess of dihydropyran containing a trace of acid to give the tetrahydropyranyl ether or diether which is then reacted with the Grignard reagent to form the acetylenic Grignard reagent. In those special cases where two hydroxyls bear a 1,2- or 1,3-relationship in the monosubstituted acetylenic compound, reaction with acetone containing a trace of acid provides a cyclic acetal which is then reacted with the Grignard reagent to form the acetylenic Grignard reagent.

Hydrolysis or conversion of the tetrahydropyranyl ether, diether or the cyclic acetal back to the desired hydroxyl(s) is accomplished by conventional means. Generally, dilute aqueous mineral acid such as hydrochloric acid is added to the isolated α-hydroxybutynoate of Formula I in the presence of a suitable solvent such as methanol and the product recovered and purified by conventional means.

Alternatively, the tetrahydropyranyl ether, diether or the cyclic acetal is hydrolyzed to the hydroxyl(s) during the simultaneous hydrolysis of the intermediate magnesium haloalkoxide in step (b) described hereinbefore through joint utilization of dilute aqueous mineral acid such as hydrochloric or sulfuric.

The monosubstituted acetylenic compounds ($R^2$—C≡C—H) of Formula IV employed as starting materials can be prepared in accordance with known or analogous methods. Generally, acetylene magnesium halide (CH≡CMgX) is reacted with a compound of the formula $R^2X$, wherein $R^2$ is defined hereinbefore and X is halogen, usually chloride, bromide or iodide. The reaction may be exemplified as follows:

(IV)

The reaction consumes reactants in the proportion of 1 mole of acetylene magnesium halide to 1 mole of $R^2X$ reactant. A suitable ratio of reactants is from about 1:1 to about 1:2 (HC≡CMgX:$R^2X$), preferably about 1:1. The reaction is usually conducted at temperatures between about 0° and about 30° C., and is ordinarily carried out under ambient pressure. The resulting reaction is usually stirred for a period of time sufficient to provide for substantial completion of the reaction, usually from about 1 to about 24 hours or more. The desired monosubstituted acetylenic compound may be recovered using conventional separatory and recovery procedures such as chromatography, distillation, recrystallization and the like.

Preformed Grignard reagents (R-MgX) wherein R is loweralkyl or aryl and X is halogen are well-known compounds to those skilled in the art. Examples of Grignard reagents include ethyl magnesium chloride ($C_2H_5MgCl$) and methyl magnesium iodide ($CH_3MgI$). The Grignard reagent is formed by the union of metallic magnesium with an organic chloride, bromide or iodide, usually in the presence of a solvent such as diethyl ether or tetrahydrofuran and under anhydrous conditions.

The α-carbonylesters of Formula III for reacting with the acetylenic Grignard reagent are of the formula:

wherein $R^1$ and $R^3$ are as previously defined. The α-carbonylesters employed as starting materials can be prepared in accordance with known methods. Generally, the α-carbonylesters, employed in preparing the compounds of the present invention, are formed by reacting a compound of the formula $R^1MgX$ with a suitable symmetrical dialkyl oxalate ($R^3OOCCOOR^3$). The reaction can be exemplified as follows:

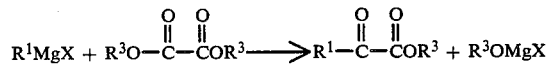

wherein $R^1$ and $R^3$ are as defined hereinbefore. The reaction generally consumes reactants in the proportions of one mole of $R^1MgX$ reactant to one mole of oxalate reactant. A suitable ratio of reactants is from about 1:1 to about 1:2 ($R^1MgX$:oxalate), preferably about 1:1. The reaction is usually conducted at temperatures between about −50° and about 20° C. and is ordinarily carried out under ambient pressure. The resulting reaction is usually stirred for a period of time sufficient to provide for substantial completion of the reaction, usually from about 1 to about 24 hours or more. Conventional separatory and recovery procedures as hereinbefore described give the desired α-carbonylester.

The following examples illustrate the present invention in a manner by which it can be practiced but, as such, should not be construed as limitations upon the overall scope of the same.

EXAMPLE 1

2-Hydroxy-7-methyl-3-octynoate, n-butyl ester

A Grignard reagent was prepared under dry nitrogen by the addition, over a 1 hour period, of a solution comprising 10.9 grams (g) (0.10 mole) of ethyl bromide is 15 milliliters (ml) of anhydrous ether to a stirred suspension of 2.4 g (0.10 g atom) of clean magnesium metal turnings in 70 ml of dry ether. Stirring at 25° C. was continued for an additional hour and then a solution of 9.6 g (0.10 mole) of 5-methyl-1-hexyne in 15 ml of dry ether was added during 30 minutes with stirring. The resulting greyish solution was then heated at reflux for 2 hours and cooled to room temperature. The solution was transferred under dry nitrogen to a 200 ml addition funnel, followed by flushing with two 15 ml portions of dry ether. This solution was then added over a 45 minute period to a stirred solution of 13.0 g (0.10 mole) of n-butyl glyoxalate in 70 ml of dry ether cooled to −20° C. The mixture was stirred at −20° C. for 2 hours and allowed to warm to room temperature overnight. The resulting yellow-orange solution was cautiously treated with 75 ml of saturated ammonium chloride solution and after stirring for 5 minutes, the two phases which formed were separated. The aqueous phase was extracted twice with 60 ml portions of ether and the combined organic phases were washed with three 75 ml portions of brine and dried over $MgSO_4$. After filtration and concentration at the stripper, the residual reddish-orange oil (18.0 g.), was fractionated through a 15 cm Vigreux column to afford, after a small forerun, a single volatile fraction, boiling point (b.p.) 107.0°–117.0° C./0.20 millimeter (mm). Redistillation of this cut provided 10.3 g (41% yield) of n-butyl 2-hydroxy-7-methyl-3-octynoate as a light yellow, sweet smelling, mobile oil, b.p. 112.0°–115.0° C./0.20 mm.

Calculated for $C_{13}H_{22}O_3$: C, 68.99; H, 9.80. Analyzed: C, 68.83; H, 9.47.

EXAMPLE 2

2-Hydroxy-2-methyl-4-phenylbutynoate, ethyl ester

A Grignard reagent was prepared under dry nitrogen by the addition over a 1 hour period of a solution comprising 10.9 g (0.10 mole) of ethyl bromide in 15 ml of anhydrous ether to a magnetically stirred suspension of 2.4 g (0.10 g atom) of clean magnesium metal turnings in 70 ml of dry ether. Stirring at 25° C. was continued for an additional hour and then a solution of 10.2 g (0.10 mole) of phenyl acetylene in 15 ml of dry ether was added over 30 minutes. The stirred solution was then heated at reflux for one hour, during which time the acetylenic Grignard reagent separated into a two phase grey-black liquid. After cooling, the two phase liquid was transferred under dry nitrogen to a 200 ml addition funnel followed by flushing with two 15 ml portions of dry ether. The contents of the funnel were rendered homogeneous, by efficient overhead mechanical stirring, and this mixture was added over 35 minutes to a magnetically stirred solution of 11.6 g (0.10 mole) of ethyl pyruvate in 80 ml of dry ether cooled to −20° C. The mixture was stirred at −20° C. for 2 hours and allowed to warm to room temperature overnight. The resulting yellow-orange solution was cautiously treated with 75 ml of saturated ammonium chloride solution and after stirring for 5 minutes, the phases were separated. The aqueous phase was extraced with two 60 ml portions of ether and the combined organic phases were washed with three 75 ml portions of brine and dried over $MgSO_4$. After filtration and concentration at the stripper, a residual reddish-orange oil (19.6 g) was fractionated through a 15 cm Vigreux column to afford, after a small forerun, a single volatile fraction, b.p. 96.0°–105.0° C./0.10 mm. Redistillation of this cut provided 8.9 g (41% yield) of ethyl-2-hydroxy-2-methyl-4-phenylbutynoate, as a colorless, viscous oil, b.p. 98.0°–101.0° C./0.05 mm.

Calculated for $C_{13}H_{14}O_3$: C, 71.54; H, 6.47. Analyzed: C, 71.20; H, 6.74.

EXAMPLE 3

2-Hydroxy-5,5-dimethyl-3-hexynoate, n-butyl ester

A Grignard reagent was prepared under dry nitrogen by the addition over a 1 hour period of a solution comprising 10.9 g (0.10 mole) of ethyl bromide in 15 ml of anhydrous ether to a mechanically stirred suspension of 2.4 g (0.10 g atom) of a clean magnesium metal turnings in 70 ml of dry ether. Stirring at 25° C. was continued for an additional hour and then a solution of 12.3 g (0.15 mole) of 3,3-dimethyl-1-butyne in 25 ml of dry ether was added during 30 minutes with stirring. The greyish solution was then heated at reflux for 2 hours during which time the acetylenic Grignard reagent separated from solution as an off-white powder. After the mixture had been cooled to −55° C., a solution of 13.0 g (0.10 mole) of n-butyl glyoxylate in 25 ml of dry ether was added during 1 minute to the rapidly stirred suspension. The mixture was maintained at −50° C. for two hours and then allowed to warm gradually overnight to room temperature. The resulting deep orange solution was then cautiously treated with 75 ml of a saturated ammonium chloride solution, and after stirring for 5 minutes, the phases were separated. The aqueous phase was extracted twice with 60 ml portions of ether and the combined organic phases washed three times with 75 ml portions of brine and were dried over $MgSO_4$. After filtration and concentration at the stripper, the residual reddish-orange oil (19.5 g.) was fractionated through a 15 cm Vigreux column to afford, after a small forerun, a single volatile fraction, b.p., 68.0°–78.0° C./0.10 mm. Refractionation of this cut provided 6.8 g (32% yield), of n-butyl 2-hydroxy-5,5-dimethyl-3-hexynoate, as a mobile, lemon-yellow oil, b.p. 72.0°–74.0° C./0.08 mm.

Calculated for $C_{12}H_{20}O_3$: C, 67.89; H, 9.50. Analyzed: C, 67.71; H, 9.21.

EXAMPLE 4

2,8-dihydroxy-3-octynoate, n-butyl ester

To 0.10 mole of ethyl magnesium bromide, prepared as above in Examples 1, 2 and 3, in diethyl ether was added over a 45 minute period, a solution comprising 18.2 g (0.10 mole) of 6-(tetrahydro-2-pyranoxy)-hex-1-yne in 25 ml of dry ether. The stirred solution was then heated at reflux for 2 hours, during which time the acetylenic magnesium bromide separated from solution as a white powder. The stirrer was stopped and the powder was scraped from the walls of the flask with a spatula under a blanket of dry nitrogen. The stirrer was again started and the suspension was cooled to −55° C. A solution of 13.0 g (0.10 mole) of freshly distilled n-butyl glyoxylate in 25 ml of dry ether was then added during 90 seconds. The mixture was then maintained at −50° C. for 2 hours and then allowed to warm gradually overnight to room temperature. The resulting yellow orange solution, containing some suspended solids, was chilled in an ice bath and cautiously treated with 100 ml of saturated ammonium chloride solution. After stirring for 15 minutes, the phases were separated and the aqueous phase was extracted twice with 60 ml portions of ether. The combined organic phases were washed with three 75 ml portions of brine and dried over MgSO$_4$. After filtration and concentration at the stripper, the residual yellow-orange oil (24.8 g) was fractionated through a 15 cm Vigreux column to afford, after a considerable low-boiling forerun, a single volatile fraction, b.p. 161.0°–164.0° C./0.25 mm. This distillate, (8.1 g) obtained as a somewhat viscous, faint yellow oil was next subjected to chromatography on 100 g of silica gel using methylene chloride/methanol, (95:5 volume/volume) as eluant, to afford 7.2 g (32% yield) of n-butyl 2,8-dihydroxy-3-octynoate, a colorless, somewhat viscous oil.

Calculated for $C_{12}H_{20}O_4$: C, 63.13; H, 8.83. Analyzed: C, 62.87; H, 8.99.

EXAMPLE 5

2-Hydroxy-5,5-dimethyl-3-hexynoic acid

A magnetically stirred mixture comprising 2.10 g (0.01 mole) of twice distilled 2-hydroxy-5,5,-dimethyl-3-hexynoate, n-butyl ester, 1.40 g (0.01 mole) of potassium carbonate and 3 ml of methanol in 20 ml of water was heated, under a dry nitrogen atmosphere, at 75°–80° C. for 1.5 hours during which time the substrate dissolved to afford a faint yellow solution. After cooling, 20 ml of water was added and the solution was exhaustively extracted with ether. The aqueous phase was then treated with 1.5 g of Darco ® activated carbon, filtered with suction through a Celite ® pad and acidified in an ice bath with 2.0 ml (0.02 mole) of concentrated hydrochloric acid. The resulting oil was extracted with three 25 ml portions of ether and the combined extracts were washed with four 35 ml portions of water and dried over MgSO$_4$. Filtration and concentration at the stripper afforded 1.20 g (75% yield) of 2-hydroxy-5,5-dimethyl-3-hexynoic acid, a light yellow, viscous oil. Pumping down at 25° C./0.20 mm for one hour produced no observable reduction in product weight.

Calculated for $C_8H_{12}O_3$: C, 61.52; H, 7.75. Analyzed: C, 61.21; H, 8.02.

EXAMPLE 6

2-Hydroxy-2-methyl-4-phenylbutynoic acid

A magnetically stirred mixture of 2.20 g (0.01 mole) of twice distilled 2-hydroxy-2-methyl-4-phenylbutynoate, ethyl ester 1.40 g (0.01 mole) of potassium carbonate and 3 ml of methanol in 20 ml of water was heated under a dry nitrogen atmosphere at 75°–80° C. for 1.5 hours, during which time the substrate dissolved to afford a faint yellow solution. After cooling, 20 ml of water was added and the solution was exhaustively extracted with ether. The aqueous phase was then treated with 1.5 g of Darco ® activated carbon, filtered with suction through a Celite ® pad and acidified in an ice bath with 2.0 ml (0.02 mole) of concentrated hydrochloric acid. The resulting oil was extracted with three 25 ml portions of ether and the combined extracts were washed with three 35 ml portions of water and dried over MgSO$_4$. Filtration and concentration at the stripper provided an almost colorless oil which solidified on cooling. Recrystallization from hexane containing a trace of ether afforded 1.60 g (89% yield) of 2-hydroxy-2-methyl-4-phenylbutynoic acid as colorless plates, m.pt. 104.5°–106.0° C.

Calculated for $C_{11}H_{10}O_3$: C, 69.46; H, 5.30. Analyzed: C, 69.53; H, 5.48.

By following the preparative procedures as set forth in the above examples and employing the appropriate starting reactants, the following compounds are prepared, as set forth in Table 1.

TABLE 1

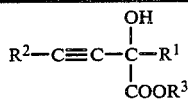

| Compound Number | R$^1$ | R$^2$ | R$^3$ | B.PT. °C./P,mm | m.p. °C. |
|---|---|---|---|---|---|
| 7 | H | n-C$_4$H$_9$ | n-C$_4$H$_9$ | 88.0–89.0/0.05 | |
| 8 | H | n-C$_4$H$_9$ | H | faint yellow oil | * |
| 9 | H | i-C$_4$H$_9$ | n-C$_4$H$_9$ | 101.0–102.0/0.10 | |
| 10 | H | i-C$_4$H$_9$ | H | faint yellow oil | * |
| 11 | H | t-C$_4$H$_9$ | n-C$_4$H$_9$ | 72.0–74.0/0.08 | |
| 12 | H | t-C$_4$H$_9$ | H | faint yellow oil | * |
| 13 | CH$_3$ | t-C$_4$H$_9$ | C$_2$H$_5$ | 46.0–48.0/0.10 | |
| 14 | CH$_3$ | t-C$_4$H$_9$ | H | | 119.5–121.0 |
| 15 | C$_2$H$_5$ | t-C$_4$H$_9$ | CH$_3$ | 52.0–54.0/0.12 | |
| 16 | C$_2$H$_5$ | t-C$_4$H$_9$ | H | | 98.0–99.5 |
| 17 | φ | t-C$_4$H$_9$ | CH$_3$ | 97.0–99.5/0.10 | |
| 18 | φ | t-C$_4$H$_9$ | H | | 123.0–124.5 |
| 19 | CH$_3$ | HOCH$_2$** | C$_2$H$_5$ | 104.0–106.0/0.10 | |
| 20 | CH$_3$ | HOCH$_2$ | H | faint yellow oil | * |
| 21 | H | HOCH$_2$(CH$_2$)$_3$** | n-C$_4$H$_9$ | 161.0–164.0/0.25 | |
| 22 | H | HOCH$_2$(CH$_2$)$_3$ | H | faint yellow oil | * |
| 23 | H | n-C$_5$H$_{11}$ | n-C$_4$H$_9$ | 93.0–94.5/0.07 | |
| 24 | H | n-C$_5$H$_{11}$ | H | faint yellow oil | * |
| 25 | H | i-C$_5$H$_{11}$ | n-C$_4$H$_9$ | 134.0–137.0/0.20 | |
| 26 | CH$_3$ | i-C$_5$H$_{11}$ | C$_2$H$_5$ | 73.0–75.0/0.17 | |
| 27 | CH$_3$ | i-C$_5$H$_{11}$ | H | | 55.5–57.0 |
| 28 | C$_2$H$_5$ | i-C$_5$H$_{11}$ | CH$_3$ | 78.0–80.0/0.10 | |
| 29 | C$_2$H$_5$ | i-C$_5$H$_{11}$ | H | faint yellow oil | * |
| 30 | φ | i-C$_5$H$_{11}$ | CH$_3$ | 121.0–123.0/0.08 | |

TABLE 1-continued $$R^2-C\equiv C-\underset{\underset{COOR^3}{|}}{\overset{\overset{OH}{|}}{C}}-R^1$$

| Compound Number | $R^1$ | $R^2$ | $R^3$ | B.PT. °C./P,mm | m.p. °C. |
|---|---|---|---|---|---|
| 31 | φ | i-C$_5$H$_{11}$ | H | faint yellow oil | * |
| 32 | CH$_3$ | φ | CH$_3$ | 108.5–110.0/0.10 | |
| 33 | CH$_3$ | φ | C$_2$H$_5$ | 98.0–101.0/0.05 | |
| 34 | CH$_3$ | φ | H | | 104.5–106.0 |
| 35 | C$_2$H$_5$ | φ | CH$_3$ | 98.0–101.0/0.05 | |
| 36 | C$_2$H$_5$ | φ | H | | 113.5–114.5 |
| 37 | φ | φ | CH$_3$ | | 79.5–80.5 |
| 38 | φ | φ | H | | 114.5–116.0 |
| 39 | CH$_3$ | CH$_3$ | H | | |
| 40 | CH$_3$ | CH$_3$ | C$_2$H$_5$ | | |
| 41 | CH$_3$ | n-C$_3$H$_7$ | H | | |
| 42 | CH$_3$ | n-C$_3$H$_7$ | C$_2$H$_5$ | | |
| 43 | CH$_3$ | iso-C$_3$H$_7$ | H | | |
| 44 | CH$_3$ | iso-C$_3$H$_7$ | C$_2$H$_5$ | | |
| 45 | CH$_3$ | n-C$_4$H$_9$ | H | | |
| 46 | CH$_3$ | n-C$_4$H$_9$ | C$_2$H$_5$ | | |
| 47 | CH$_3$ | iso-C$_4$H$_9$ | H | | |
| 48 | CH$_3$ | iso-C$_4$H$_9$ | C$_2$H$_5$ | | |
| 49 | CH$_3$ | tert-C$_4$H$_9$ | H | | |
| 50 | CH$_3$ | tert-C$_4$H$_9$ | C$_2$H$_5$ | | |
| 51 | CH$_3$ | n-C$_5$H$_{11}$ | H | | |
| 52 | CH$_3$ | n-C$_5$H$_{11}$ | C$_2$H$_5$ | | |
| 53 | CH$_3$ | iso-C$_5$H$_{11}$ | H | | |
| 54 | CH$_3$ | iso-C$_5$H$_{11}$ | C$_2$H$_5$ | | |
| 55 | CH$_3$ | neo-C$_5$H$_{11}$ | H | | |
| 56 | CH$_3$ | neo-C$_5$H$_{11}$ | C$_2$H$_5$ | | |
| 57 | CH$_3$ | cyclopropyl | H | | |
| 58 | CH$_3$ | cyclopropyl | C$_2$H$_5$ | | |
| 59 | CH$_3$ | cyclobutyl | H | | |
| 60 | CH$_3$ | cyclobutyl | C$_2$H$_5$ | | |
| 61 | CH$_3$ | cyclopentyl | H | | |
| 62 | CH$_3$ | cyclopentyl | C$_2$H$_5$ | | |
| 63 | CH$_3$ | cyclohexyl | H | | |
| 64 | CH$_3$ | cyclohexyl | C$_2$H$_5$ | | |
| 65 | CH$_3$ | φ | H | | |
| 66 | CH$_3$ | φ | C$_2$H$_5$ | | |
| 67 | CH$_3$ | φOCH$_3$(2) | H | | |
| 68 | CH$_3$ | φOCH$_3$(2) | C$_2$H$_5$ | | |
| 69 | CH$_3$ | φOCH$_3$(3) | H | | |
| 70 | CH$_3$ | φOCH$_3$(3) | C$_2$H$_5$ | | |
| 71 | CH$_3$ | φOCH$_3$(4) | H | | |
| 72 | CH$_3$ | φOCH$_3$(4) | C$_2$H$_5$ | | |
| 73 | CH$_3$ | φ(OCH$_3$)$_2$(2,3) | H | | |
| 74 | CH$_3$ | φ(OCH$_3$)$_2$(2,3) | C$_2$H$_5$ | | |
| 75 | CH$_3$ | φ(OCH$_3$)$_2$(2,4) | H | | |
| 76 | CH$_3$ | φ(OCH$_3$)$_2$(2,4) | C$_2$H$_5$ | | |
| 77 | CH$_3$ | φ(OCH$_3$)$_2$(2,5) | H | | |
| 78 | CH$_3$ | φ(OCH$_3$)$_2$(2,5) | C$_2$H$_5$ | | |
| 79 | CH$_3$ | φ(OCH$_3$)$_2$(2,6) | H | | |
| 80 | CH$_3$ | φ(OCH$_3$)$_2$(2,6) | C$_2$H$_5$ | | |
| 81 | CH$_3$ | φ(OCH$_3$)$_2$(3,4) | H | | |
| 82 | CH$_3$ | φ(OCH$_3$)$_2$(3,4) | C$_2$H$_5$ | | |
| 83 | CH$_3$ | φ(OCH$_3$)$_2$(3,5) | H | | |
| 84 | CH$_3$ | φ(OCH$_3$)$_2$(3,5) | C$_2$H$_5$ | | |
| 85 | CH$_3$ | φ(OCH$_3$)$_3$(2,4,6) | H | | |
| 86 | CH$_3$ | φ(OCH$_3$)$_3$(2,4,6) | C$_2$H$_5$ | | |
| 87 | CH$_3$ | φ(OCH$_3$)$_3$(2,3,4) | H | | |
| 88 | CH$_3$ | φ(OCH$_3$)$_3$(2,3,4) | C$_2$H$_5$ | | |
| 89 | CH$_3$ | φ(OCH$_3$)$_3$(2,3,5) | H | | |
| 90 | CH$_3$ | φ(OCH$_3$)$_3$(2,3,5) | C$_2$H$_5$ | | |
| 91 | CH$_3$ | φ(OCH$_3$)$_3$(2,3,6) | H | | |
| 92 | CH$_3$ | φ(OCH$_3$)$_3$(2,3,6) | C$_2$H$_5$ | | |
| 93 | CH$_3$ | φ(OCH$_3$)$_3$(3,4,5) | H | | |
| 94 | CH$_3$ | φ(OCH$_3$)$_3$(3,4,5) | C$_2$H$_5$ | | |
| 95 | CH$_3$ | φCl(2) | H | | |
| 96 | CH$_3$ | φCl(2) | C$_2$H$_5$ | | |
| 97 | CH$_3$ | φCl(3) | H | | |
| 98 | CH$_3$ | φCl(3) | C$_2$H$_5$ | | |
| 99 | CH$_3$ | φCl(4) | H | | |
| 100 | CH$_3$ | φCl(4) | C$_2$H$_5$ | | |
| 101 | CH$_3$ | φCl(2,3) | H | | |
| 102 | CH$_3$ | φCl(2,3) | C$_2$H$_5$ | | |
| 103 | CH$_3$ | φCl$_2$(2,4) | H | | |
| 104 | CH$_3$ | φCl$_2$(2,4) | C$_2$H$_5$ | | |

TABLE 1-continued $$R^2-C\equiv C-\underset{\underset{COOR^3}{|}}{\overset{\overset{OH}{|}}{C}}-R^1$$

| Compound Number | R¹ | R² | R³ | B.PT. °C./P,mm | m.p. °C. |
|---|---|---|---|---|---|
| 105 | $CH_3$ | $\phi Cl_2(2,5)$ | H | | |
| 106 | $CH_3$ | $\phi Cl_2(2,5)$ | $C_2H_5$ | | |
| 107 | $CH_3$ | $\phi Cl_2(2,6)$ | H | | |
| 108 | $CH_3$ | $\phi Cl_2(2,6)$ | $C_2H_5$ | | |
| 109 | $CH_3$ | $\phi Cl_2(3,4)$ | H | | |
| 110 | $CH_3$ | $\phi Cl_2(3,4)$ | $C_2H_5$ | | |
| 111 | $CH_3$ | $\phi Cl_2(3,5)$ | H | | |
| 112 | $CH_3$ | $\phi Cl_2(3,5)$ | $C_2H_5$ | | |
| 113 | $CH_3$ | $\phi Cl_3(2,4,6)$ | H | | |
| 114 | $CH_3$ | $\phi Cl_3(2,4,6)$ | $C_2H_5$ | | |
| 115 | $CH_3$ | $\phi Cl_3(2,3,4)$ | H | | |
| 116 | $CH_3$ | $\phi Cl_3(2,3,4)$ | $C_2H_5$ | | |
| 117 | $CH_3$ | $\phi Cl_3(2,3,5)$ | H | | |
| 118 | $CH_3$ | $\phi Cl_3(2,3,5)$ | $C_2H_5$ | | |
| 119 | $CH_3$ | $\phi Cl_3(2,3,6)$ | H | | |
| 120 | $CH_3$ | $\phi Cl_3(2,3,6)$ | $C_2H_5$ | | |
| 121 | $CH_3$ | $\phi Cl_3(3,4,5)$ | H | | |
| 122 | $CH_3$ | $\phi Cl_3(3,4,5)$ | $C_2H_5$ | | |
| 123 | $CH_3$ | $\phi F(2)$ | H | | |
| 124 | $CH_3$ | $\phi F(2)$ | $C_2H_5$ | | |
| 125 | $CH_3$ | $\phi F(3)$ | H | | |
| 126 | $CH_3$ | $\phi F(3)$ | $C_2H_5$ | | |
| 127 | $CH_3$ | $\phi F(4)$ | H | | |
| 128 | $CH_3$ | $\phi F(4)$ | $C_2H_5$ | | |
| 129 | $CH_3$ | $\phi F_2(2,3)$ | H | | |
| 130 | $CH_3$ | $\phi F_2(2,3)$ | $C_2H_5$ | | |
| 131 | $CH_3$ | $\phi F_2(2,4)$ | H | | |
| 132 | $CH_3$ | $\phi F_2(2,4)$ | $C_2H_5$ | | |
| 133 | $CH_3$ | $\phi F_2(2,5)$ | H | | |
| 134 | $CH_3$ | $\phi F_2(2,5)$ | $C_2H_5$ | | |
| 135 | $CH_3$ | $\phi F_2(2,6)$ | H | | |
| 136 | $CH_3$ | $\phi F_2(2,6)$ | $C_2H_5$ | | |
| 137 | $CH_3$ | $\phi F_2(3,4)$ | H | | |
| 138 | $CH_3$ | $\phi F_2(3,4)$ | $C_2H_5$ | | |
| 139 | $CH_3$ | $\phi F_2(3,5)$ | H | | |
| 140 | $CH_3$ | $\phi F_2(3,5)$ | $C_2H_5$ | | |
| 141 | $CH_3$ | $\phi F_3(2,4,6)$ | H | | |
| 142 | $CH_3$ | $\phi F_3(2,4,6)$ | $C_2H_5$ | | |
| 143 | $CH_3$ | $\phi F_3(2,3,4)$ | H | | |
| 144 | $CH_3$ | $\phi F_3(2,3,4)$ | $C_2H_5$ | | |
| 145 | $CH_3$ | $\phi F_3(2,3,5)$ | H | | |
| 146 | $CH_3$ | $\phi F_3(2,3,5)$ | $C_2H_5$ | | |
| 147 | $CH_3$ | $\phi F_3(2,3,6)$ | H | | |
| 148 | $CH_3$ | $\phi F_3(2,3,6)$ | $C_2H_5$ | | |
| 149 | $CH_3$ | $\phi F_3(3,4,5)$ | H | | |
| 150 | $CH_3$ | $\phi F_3(3,4,5)$ | $C_2H_5$ | | |
| 151 | $CH_3$ | $\phi Br(2)$ | H | | |
| 152 | $CH_3$ | $\phi Br(2)$ | $C_2H_5$ | | |
| 153 | $CH_3$ | $\phi Br(3)$ | H | | |
| 154 | $CH_3$ | $\phi Br(3)$ | $C_2H_5$ | | |
| 155 | $CH_3$ | $\phi Br(4)$ | H | | |
| 156 | $CH_3$ | $\phi Br(4)$ | $C_2H_5$ | | |
| 157 | $CH_3$ | $\phi Br_2(2,3)$ | H | | |
| 158 | $CH_3$ | $\phi Br_2(2,3)$ | $C_2H_5$ | | |
| 159 | $CH_3$ | $\phi Br_2(2,4)$ | H | | |
| 160 | $CH_3$ | $\phi Br_2(2,4)$ | $C_2H_5$ | | |
| 161 | $CH_3$ | $\phi Br_2(2,5)$ | H | | |
| 162 | $CH_3$ | $\phi Br_2(2,5)$ | $C_2H_5$ | | |
| 163 | $CH_3$ | $\phi Br_2(2,6)$ | H | | |
| 164 | $CH_3$ | $\phi Br_2(2,6)$ | $C_2H_5$ | | |
| 165 | $CH_3$ | $\phi Br_2(3,4)$ | H | | |
| 166 | $CH_3$ | $\phi Br_2(3,4)$ | $C_2H_5$ | | |
| 167 | $CH_3$ | $\phi Br_2(3,5)$ | H | | |
| 168 | $CH_3$ | $\phi Br_2(3,5)$ | $C_2H_5$ | | |
| 169 | $CH_3$ | $\phi Br_3(2,4,6)$ | H | | |
| 170 | $CH_3$ | $\phi Br_3(2,4,6)$ | $C_2H_5$ | | |
| 171 | $CH_3$ | $\phi Br_3(2,3,4)$ | H | | |
| 172 | $CH_3$ | $\phi Br_3(2,3,4)$ | $C_2H_5$ | | |
| 173 | $CH_3$ | $\phi Br_3(2,3,5)$ | H | | |
| 174 | $CH_3$ | $\phi Br_3(2,3,5)$ | $C_2H_5$ | | |
| 175 | $CH_3$ | $\phi Br_3(2,3,6)$ | H | | |
| 176 | $CH_3$ | $\phi Br_3(2,3,6)$ | $C_2H_5$ | | |
| 177 | $CH_3$ | $\phi Br_3(3,4,5)$ | H | | |
| 178 | $CH_3$ | $\phi Br_3(3,4,5)$ | $C_2H_5$ | | |

TABLE 1-continued $$R^2-C\equiv C-\underset{\underset{COOR^3}{|}}{\overset{\overset{OH}{|}}{C}}-R^1$$

| Compound Number | R¹ | R² | R³ | B.PT. °C./P,mm | m.p. °C. |
|---|---|---|---|---|---|
| 179 | CH₃ | φCF₃(2) | H | | |
| 180 | CH₃ | φCF₃(2) | C₂H₅ | | |
| 181 | CH₃ | φCF₃(3) | H | | |
| 182 | CH₃ | φCF₃(3) | C₂H₅ | | |
| 183 | CH₃ | φCF₃(4) | H | | |
| 184 | CH₃ | φCF₃(4) | C₂H₅ | | |
| 185 | CH₃ | φ(CF₃)₂(2,3) | H | | |
| 186 | CH₃ | φ(CF₃)₂(2,3) | C₂H₅ | | |
| 187 | CH₃ | φ(CF₃)₂(2,4) | H | | |
| 188 | CH₃ | φ(CF₃)₂(2,4) | C₂H₅ | | |
| 189 | CH₃ | φ(CF₃)₂(2,5) | H | | |
| 190 | CH₃ | φ(CF₃)₂(2,5) | C₂H₅ | | |
| 191 | CH₃ | φ(CF₃)₂(2,6) | H | | |
| 192 | CH₃ | φ(CF₃)₂(2,6) | C₂H₅ | | |
| 193 | CH₃ | φ(CF₃)₂(3,4) | H | | |
| 194 | CH₃ | φ(CF₃)₂(3,4) | C₂H₅ | | |
| 195 | CH₃ | φ(CF₃)₂(3,5) | H | | |
| 196 | CH₃ | φ(CF₃)₂(3,5) | C₂H₅ | | |
| 197 | CH₃ | φ(CF₃)₃(2,4,6) | H | | |
| 198 | CH₃ | φ(CF₃)₃(2,4,6) | C₂H₅ | | |
| 199 | CH₃ | φ(CF₃)₃(2,3,4) | H | | |
| 200 | CH₃ | φ(CF₃)₃(2,3,4) | C₂H₅ | | |
| 201 | CH₃ | φ(CF₃)₃(2,3,5) | H | | |
| 202 | CH₃ | φ(CF₃)₃(2,3,5) | C₂H₅ | | |
| 203 | CH₃ | φ(CF₃)₃(2,3,6) | H | | |
| 204 | CH₃ | φ(CF₃)₃(2,3,6) | C₂H₅ | | |
| 205 | CH₃ | φ(CF₃)₃(3,4,5) | H | | |
| 206 | CH₃ | φ(CF₃)₃(3,4,5) | C₂H₅ | | |

*Purified as potassium salt
**Protected as tetrahydropyranyl ether during Grignard addition
***For compounds 67-206 the bracketed portion in the column for R² represents the position of the substituents on the phenyl (φ) ring. For example, in compound number 73, wherein R² is φ(OCH₃)₂(2,3,), the —OCH₃ substituents are located at the 2 and 3 positions on the phenyl ring.

The following examples exemplify the preparation of various starting materials used to make the present invention.

EXAMPLE 207 n-Butyl Glyoxylate

A mechanically stirred solution of 65.0 g (0.25 mole) of di-n-butyl-d-tartrate in 250 ml of dry benzene was maintained at 30° C. (cold water bath), while 116.0 g (0.27 mole) of lead tetraacetate was added in portions during 30 minutes. After addition was complete, the mixture was stirred for one hour at room temperature, during which time the gummy salts became crystalline. The salts were then removed by filtration at the pump and were washed with 100 ml of benzene. The benzene and most of the acetic acid were removed at the stripper and the residue was distilled at reduced pressure through a 15 cm Vigreux column, the fraction boiling between 60°-76° C. at 15 mm being collected. Careful refractionation of this material afforded 46.0 g (71% yield) of heart cut n-butyl glyoxylate as a colorless, somewhat viscous oil, b.pt. 65.0-67.0/18.0 mm. This substance should be utilized as soon as possible following preparation and should be stored under nitrogen.

A 2,4-dinitrophenylhydrazone was obtained as golden yellow needles having a felt-like texture, from aqueous methanol, m.pt. 115.5°-117.0° C.

Calculated for $C_{12}H_{14}N_4O_6$: C, 46.45; H, 4.55; N, 18.06. Analyzed: C, 46.42; H, 4.77; N, 17.96.

EXAMPLE 208

Tetrahydropyranyl ether protection of 1-hexyn-6-ol

A magnetically stirred mixture of 29.4 g (0.30 mole) of freshly distilled 1-hexyn-6-Ol and 30.3 g (0.36 mole) of freshly distilled 2,3-dihydropyran was chilled in an ice bath and 200 mg of concentrated hydrochloric acid was added in one portion. After the initial exotherm had subsided the cooling bath was removed and the mixture was stirred under dry nitrogen overnight. It was then cautiously poured, with stirring, into 125 ml of 5 percent aqueous sodium hydroxide solution. The organic phase was extracted with three 50 ml portions of ether and the combined ether phases were washed with three 35 ml portions of brine and dried over MgSO₄. After filtration and concentration at the stripper (bath ≈50° C.), the residual oil was fractionated through a 15 cm Vigreux column to provide, after a negligible forerun 49.1 g (90% yield) of 6-(tetrahydro-2-pyranoxy)hex-1-yne, as a colorless, sweet smelling, mobile oil, b.pt. 115.0°-117.0° C./10 mm.

The compounds of the present invention are useful as plant growth regulators for enhancing photosynthesis. The properties of these compounds for increasing photosynthesis in plants can be demonstrated by contacting a plant with the subject compounds, whose application may be either preemergent or postemergent, preferably postemergent.

In particular, it has been discovered that the photosynthesis in plants can be enhanced by contacting such plants and/or their habitats with compositions containing an amount effective to increase photosynthesis in plants of at least one of the α-hydroxybutynoic compounds disclosed herein. When the terrestial plant species are contacted with compositions containing one or more of the α-hydroxybutynoic compounds in dosages sufficient to supply from about 0.01 to about 10.0 pounds (lb) of the compound per acre, an acceptable enhancement rate of photosynthesis in such plants can be obtained: The α-hydroxybutynoic compounds can be applied to plants either during their vegetative or their flowering stage, preferably during their flowering stage. For example, the hydroxybutynoic compounds can be applied to plant parts during vegetative stages such as during their first trifoliate leaf stage (broad leaf plants in the case of beans) or during podding or seed filling stage of flowering. Preferably, the hydroxybutynoic compounds are applied at a rate of 0.25 to 8 lb/acre, more preferably from about 0.25 to about 1.0 lb/acre.

Not all the compounds of the present invention are equally effective in enhancing photosynthesis. When applied to the same plant species, some compounds are more effective at a lower dosage rate than are other compounds.

The application to plants, plant-parts, rooting zones and/or their habitats of a composition containing an amount effective to increase photosynthesis in plants of an α-hydroxybutynoic compound is essential and critical for the practice of the present invention. The exact dosage to be supplied by the composition in a given operation is dependent upon the plant species and upon the stage of growth and hardiness thereof as well as upon the plant part to be exposed to the composition. Other factors, such as for example, weather, bacteria and other organisms found in the soil must also be considered.

Compositions comprising an α-hydroxybutynoic compound with an inert material known as an agricultural adjuvant or carrier in solid or liquid form allow proper application of an effective amount of the active ingredient. The α-hydroxybutynoic compounds are mixed in such quantity of ultimate treating material that adequate coverage of all plants and plant-parts or adequate admixture with their habitats (e.g., soil) can be obtained. An adjuvant is defined herein as any substance in a formulation or added to the formulation to improve activity or application characteristics to the plant parts. Good results are obtained when employing a carrier material in relatively small, but effective amounts. Generally, however, the best results are obtained by employing either a surface wetting agent, in an amount sufficient to emulsify the α-hydroxybutynoic compound or using small amounts of an organic solvent with water as a carrier, for example, in an amount which the α-hydroxybutynoic compound represents from 50–99 percent by weight, of the total treating material. Such agents provide proper intimate contact of the α-hydroxybutynoic compound with the plant.

The exact concentration of the α-hydroxybutynoic compounds employed in the compositions for application to plants, plant-parts and/or their habitats is not critical and can vary considerably provided the required dosage of effective agent is supplied to the plant, plant-part, rooting agent, and/or habitat treated. The concentration of the α-hydroxybutynoic compound in liquid compositions employed to supply the desired dosage generally is from about 0.01 to about 50 percent by weight, preferably from about 12 to about 50 percent, although concentrations as high as 96 percent by weight can be conveniently employed. In finely divided solid carrier compositions, the concentration of the α-hydroxybutynoic compound can be from 0.1 to 60 percent by weight. In compositions to be employed as concentrates, the α-hydroxybutynoic compound can be present in a concentration of from about 5 to about 98 percent by weight.

Liquid compositions employed as a spray containing the desired amount of active ingredient can be prepared by dissolving the α-hydroxybutynoic compound in a small amount of an organic liquid carrier or by dispersing the α-hydroxybutynoic compound in water with or without the aid of a suitable surface wetting agent such as an ionic or non-ionic emulsifying agent. The aqueous compositions can contain one or more water immiscible solvents for the α-hydroxybutynoic compound. In such compositions, the carrier comprises an aqueous emulsion, i.e., a mixture of water, emulsifying agent and a low concentration of a water miscible solvent. The choice of dispersing and emulsifying agent and the amount thereof employed is dictated by the nature of the composition and by the ability of the agent to facilitate the dispersion of the α-hydroxybutynoic compound in the carrier to produce the desired composition. Dispersing and emulsifying agents which can be employed in the compositions include the condensation products of alkylene oxides with phenols and organic acids, alkyl aryl sulfonates, polyoxyalkylene derivatives of sorbitan esters, complex ether alcohols, mahogany soaps, and the like.

In the preparation of dust compositions, the active ingredient is dispersed in and on a finely divided solid carrier such as clay, talc, chalk, gypsum, bentonite, fuller's earth, attapulgite, and the like. In such operation, the finely divided carrier is mechanically mixed or ground with the α-hydroxybutynoic compound. Depending upon the proportion of ingredients, these dust compositions can be employed as concentrates and subsequently diluted with additional solid carrier or with liquid or solid surface-wetting agents to obtain the desired amount of active ingredient in a composition adapted to be employed for the enhancement of photosynthesis in the plants. Also, such dust compositions, particularly when finely ground or milled, can be dispersed in water, preferably with the aid of a surface-wetting agent, to form spray mixtures.

Suitable adjuvants useful in making up compositions of the foregoing type are well known to those skilled in the art. The methods of applying the solid or liquid formulations similarly are well known to the skilled artisan.

Satisfactory results are obtained when the α-hydroxybutynoic compositions are combined with other agricultural materials intended to be applied to plants, plant-parts and/or their habitats. Such materials include fertilizers, fungicides, insecticides, acaricides, nematocides, bactericides, soil conditioning agents, other herbicides, and the like.

When operating in accordance with the present invention, compositions containing amounts effective to enhance photosynthesis in plants of the α-hydroxybutynoic compounds are applied to plants, plant-parts and/or their habitats in any convenient fashion. Applications to a plant habitat, e.g., soil, can be carried out by simply mixing with the habitat, such as by applying to the surface of soil by spraying a liquid composition and thereafter dragging or discing into the soil to the desired depth or by employing a liquid carrier to accomplish the penetration and impregnation. The application of spray and dust compositions to the surface of soil can be carried out by conventional methods, e.g., power dusters, boom and hand sprayers and spray dusters.

In a further method, the distribution of the α-hydroxybutynoic compositions in soil can be accomplished by introducing the active ingredient in the water employed to irrigate the soil. In such procedures, the amount of water can be varied with the porosity and water holding capacity of the soil to obtain a desired depth of distribution of the agent.

In addition, the present method also comprehends the employment of an aerosol composition containing an α-hydroxybutynoic compound as an active compound. Such a composition is prepared according to conventional methods whereiin the active ingredient is dispersed in a solvent, and the resultant dispersion mixed with a readily volatilized liquid propellant. Such variables as the particle active ingredient to be used and the particular plant part to be treated with determine the identity of the solvent and the concentration of the active ingredient therein. Examples of suitable solvents are water, and low concentrations of an organic solvent such as acetone, isopropanol, and 2-ethoxyethanol. Also, employment of the α-hydroxybutynoic compound in pastes, gels, foams, invert emulsions, and the like, as well as pigmented or unpigmented pelleted solids is contemplated.

The following examples further illustrate the present invention.

In the test method of the whole part assay to follow, compounds that were insoluble were ultrasonicated, creating a fine suspension or, in some cases, an emulsion, for subsequent foliar application. The system for measuring carbon dioxide consumed by the plant was modified from that used by Harris et al., *Measurement of $CO_2$ and $H_2O$ Vapor Exchange in Spinach Leaf Discs* (1983), Plant Physiol., 71, pages 102–107. Generally, the system was made of a source of illumination, a transparent leaf chamber, a source of carbon dioxide and oxygen, and an analyzer for measuring carbon dioxide entering and exiting the leaf chamber.

The transparent leaf chamber for measuring both $CO_2$ (photosynthesis) and $H_2O$ vapor (transpiration) in attached leaves was designed to be portable and hand-held. The chamber was made of two circular halves, an upper and a lower half constructed for clear Perspex ® plastic. Each half had a crescent shaped series of inlets and outlets allowing for uniform flow of gases over the sandwiched leaf disc surface. Each inlet diameter was 3–4 fold smaller than that of the outlets to reduce the possibility of any pressure build-up. Since the volume of the chamber was small and the gas inlets were aimed at a 45° angle towards the leaf surface, the boundary layer resistance was minimal and allowed for fast, accurate photosynthesis measurements. Both halves were held together by means of a hand-applied spring clamp which exerted enough pressure for a leak-proof sandwiching without harming the leaf. The inner chamber diameter measured 4 cm.

EXAMPLE 10

Whole Plant Assay (Test Method)

Representative α-hydroxybutynoic compounds of the present invention were evaluated using whole bush bean plants. In these evaluations, bush bean plants were grown to the first trifoliate stage, when three leaflets per branch appeared. Aqueous solutions containing the α-hydroxybutynoic compounds in concentrations of 4, 10, 40, 400, and 1000 ppm, respectively were applied to bush bean plants, two plants per concentration. The spray compositions were made by mixing the active ingredient in water which contained 0.1 percent by volume of Tween ® 20 surfactant (Tween ® is a trademark of the Atlas Chemical Company). The applications to the plants were made to the point of run-off and was carried out using conventional spraying equipment. Control pants were sprayed with similar compositions not containing the α-hydroxybutynoic compounds. Two weeks after spraying, the rates of photosynthesis of the unifoliate, the first trifoliate and the subsequently emerged second trifoliate leaves were measured while the leaves were attached to the plant.

The leaf chamber was illuminated by means of a Leitz Prado Universal projector positioned 11 inches away. The unfocused light beam was reflected down onto the leaf surface by means of an overhead mirror. This system gave light intensities of $1.0 \times 7 \times 10^3$ μ Einsteins·m$^{-2}$·s$^{-1}$. Two Westinghouse low temperature flood lamps (150 W) were used to illuminate the rest of the plant to reduce a sink-source effect and to preequilibrate test leaves to a steady state rate of photosynthesis for quicker measurements.

Prior to the measurements of photosynthesis, the bush bean plants under study were transferred from the adjacent greenhouse into the laboratory. One of the unifoliate leaves, or the central leaflet of the trifoliate leaf, was then sandwiched between the two halves of the leaf chamber and clamped to make it air-tight. Gas (350 ppm $CO_2$, 21 percent $O_2$, balance $N_2$) was then passed over both surfaces of the leaf and out to precalibrated IRGA's. Both the plant under study and the chamber were then illuminated. The leaf remained in the photosynthesis chamber until the IRGA traces stabilized to a steady-state condition and the recorder outputs were noted. The recorder was adjusted so that the IRGA's signal output gave near a full-scale recorder deflection under a steady-state condition.

The resistances to $CO_2$ and $H_2O$ vapor diffusion were calculated using an electrical analogy and the results were processed by means of an Epson computer with a program written by Dr. Gary Harris, Wellesley College. After known amounts of carbon dioxide and oxygen had been passed over both sides of the leaf from the carbon dioxide and oxygen sources, the analyzer measured the differences in the amounts of carbon dioxide entering and exiting the leaf chamber. A decrease in the amount of carbon dioxide exiting the leaf chamber by leaves receiving the α-hydroxyacetylenic compounds as compared to the controls indicated a net increase in the rate of photosynthesis. The results of the evaluation of the treated plants are set forth below in Table 2.

Substantially the same fine results are obtained upon application of other compounds of the present invention to plants according to the procedures hereinbefore described.

TABLE 2

$$R^2-C\equiv C-\underset{\underset{COOR^3}{|}}{\overset{\overset{OH}{|}}{C}}-R^1$$

| | | | | Percent Increase in Rate of Photosynthesis in the | | |
|---|---|---|---|---|---|---|
| $R^1$ | $R^2$ | $R^3$ | Dosage Rate ppm | Unifoliate Leaf | First Trifoliate Leaf | Second Trifoliate Leaf |
| H | iso-$C_5H_{11}$ | H | 0 | 0.0 | 0.0 | 0.0 |
| | | | 4 | 0.0 | 13.0 | 6.9 |
| | | | 10 | 0.0 | 14.8 | 24.6 |
| | | | 40 | 14.3 | 38.0 | 30.1 |
| | | | 400 | 24.3 | 44.2 | 54.8 |
| | | | 1000 | 30.4 | 75.1 | 63.0 |
| $CH_3$ | iso-$C_5H_{11}$ | H | 0 | — | 0.0 | 0.0 |
| | | | 4 | — | 23.8 | 36.6 |
| | | | 10 | — | 56.0 | 34.6 |
| | | | 40 | — | 48.0 | 44.5 |
| | | | 400 | — | 30.3 | 37.6 |
| | | | 1000 | — | 54.0 | 29.7 |
| $CH_3$ | φ | H | 0 | 0.0 | 0.0 | 0.0 |
| | | | 4 | 24.8 | 8.4 | 7.1 |
| | | | 10 | 62.4 | 27.1 | 33.9 |
| | | | 40 | 237.6 | 50.8 | 85.7 |
| | | | 400 | 181.2 | 71.0 | 78.5 |
| | | | 1000 | 131.2 | 77.9 | 64.2 |

"—" indicates the percent increase could not be calculated without data for the control.

A plant enzyme assay using glycolate oxidase was employed to test the compounds of the present invention. The assay was modified from the procedure used in Kerr et al. (1975), *Purification and Properties of Glycolate Oxidase from Pisum Sativium Leaves,* Phytochemistry, 14, pages 359-362. The enzyme, glycolate oxidase, is believed to catalyze the conversion of glycolic acid (a primary and essential substrate in photorespiration) to glyoxylate (another essential intermediate in photorespiration). This conversion is believed to be the first step in photorespiration. Inhibiting glycolate oxidase will close down or at least retard photorespiration (which has no known useful function in plant life) and thus conserve the carbon which would otherwise be lost as carbon dioxide. With more carbon available to the plant, the rate of photosynthesis will be enhanced.

The oxygen electrode within which the plant enzyme assay is conducted has a cap with an inlet port through which the requisite chemical reagents can be added and an electrode for measuring the rates of oxygen consumption. Oxygen electrodes are known to one skilled in the art.

Generally, in the plant enzyme assay, an α-hydroxybutynoic compound is added to a buffered plant extract containing glycolate oxidase and any changes in oxygen consumption or uptake in the buffered solution are measured with the oxygen electrode. A decrease in the rate with which oxygen is consumed in treatments receiving the α-hydroxyacetylenic compound compared to the controls indicates an inhibition of the glycolate oxidase enzyme.

The final concentration of the α-hydroxybutynoic compounds is generally between about 0.5 mM to 50 mM. Generally, the reaction is conducted at ambient pressures and maintained at temperatures of about 30° C. The solution is stirred throughout the course of the assay and the assay is conducted necessarily in the dark to prevent photooxidation of the flavin mononucleotide (FMN), a co-factor of glycolate oxidase. FMN is believed to supply electrons for driving the reaction for converting glycolate to glyoxylate. Sodium azide is used to inhibit residual catalase activity.

EXAMPLE 11

Plant Enzyme Assay (Test Method)

An enzyme extract was prepared by homogenizing 5 g of spinach leaves in 20 ml of 0.1 molar (M) Tris-HCl buffer (ice cold) set to a pH of 8.3 in a blender for about two minutes. The homogenate from the blender was strained through four layers of cheesecloth and centrifuged at 19,000 revolutions per minute (rpm) for 15 minutes at 4° C. The clear supernatant containing glycolate oxidase, obtained after filtering and centrifugation, was the enzyme extract used for the subsequent plant enzyme assays. Enzyme extracts were stored at 4° C. until used.

The enzyme assays were carried out in an oxygen electrode maintained at a temperature of 30° C. The reaction mixtures (2 ml) were prepared by adding 100 millimolar (mM) tris-HCl buffer, 60 micromolar (μM) flavin mononucleotide (FMN), 1 mM sodium azide, and 0.1 ml of the enzyme preparation. The reaction was initiated by adding 15 mM of sodium glycolate and was run for 10 minutes. Light was excluded from the oxygen electrode containing the reaction mixture. The results of the plant enzyme assay are provided in Table 3. Values can range from 0 to −100, where 0 indicates no inhibition and −100 indicates total inhibition.

TABLE 3

Inhibition of Glycolate Oxidase by α-Hydroxybutynoic Compounds $$R^2-C\equiv C-\underset{\underset{COOR^3}{|}}{\overset{\overset{OH}{|}}{C}}-R^1$$

| Compound Tested | | | Dosage in mM | Percent Inhibition of Glycolate Oxidase |
|---|---|---|---|---|
| $R^1$ | $R^2$ | $R^3$ | | |
| $CH_3$ | $CH_2OH$ | H | 50.0 | −20 |
| $CH_3$ | $CH_2OH$ | $CH_2CH_3$ | 50.0 | −30 |
| $CH_3$ | $(CH_2)_2CH(CH_3)_2$ | H | 12.5 | −40 |
| $CH_3$ | $C_6H_5$ | H | 25.0 | −45 |

What is claimed is:

1. A method for increasing photosynthesis in plants comprising applying to the locus of said plants an amount effective to increase photosynthesis in plants of a compound of the formula

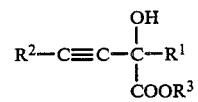

wherein
$R^1$ represents
(a) loweralkyl,
(b) hydroxyloweralkyl,
(c) substituted cycloalkyl of the formula:

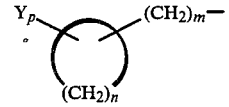

wherein m is an integer from 0 to 4;
n is an integer from 3 to 6;
p is an integer from 0 to the maximum number of positions remaining on the cycloalkyl;
Y is hydrogen,
loweralkyl,
loweralkoxy,
halogen,
—CF$_3$,
aryl or
acetal of the formula:

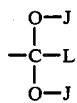

wherein
J is loweralkyl and
L is hydrogen, loweralkyl, cycloalkyl or substituted cycloalkyl of the formula:

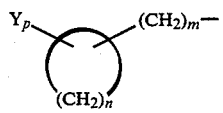

wherein
m is an integer from 0 to 4;
n is an integer from 3 to 6;
p is an integer from 0 to the maximum number of positions remaining on the cycloalkyl;
Y is hydrogen,
loweralkyl,
loweralkoxy,
halogen,
—CF$_3$,
aryl or
acetal of the formula:

wherein
J is loweralkyl and
L is hydrogen, loweralkyl or cycloalkyl;
(d) aryl or
(e) substituted aralkyl of the formula

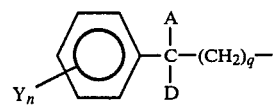

wherein
q is an integer from 0 to 6;
A and D represent hydrogen,
loweralkyl or
loweralkoxy; and
Y and n are defined as hereinbefore;
$R^2$ represents $R^1$ or hydrogen; and $R^3$ represents hydrogen or loweralkyl, or counterion of amine, ammonium, sodium, potassium, calcium or magnesium.

2. The method of claim 1 wherein $R^1$ is methyl.
3. The method of claim 1 wherein $R^1$ is methyl and $R^2$ is phenyl.
4. The method of claim 1 wherein $R^1$ is loweralkyl.
5. The method of claim 4 wherein $R^2$ is iso-$C_5H_{11}$.
6. The method of claim 1 wherein $R^1$ and $R^2$ are phenyl.
7. The method of claim 1 wherein $R^2$ is hydroxyloweralkyl.
8. The method of claim 7 wherein $R^2$ is $CH_2OH$.
9. The method of claim 1 wherein $R^1$ is $C_2H_5$ and $R^2$ is tert-$C_4H_9$.
10. The method of claim 1 wherein $R^1$ is methyl and $R^2$ is phenyl.
11. The method of claim 1 wherein $R^1$ is methyl and $R^2$ is tert-$C_4H_9$.
12. The method of claim 1 wherein $R^3$ is a cation selected from the group consisting of amine, ammonium, sodium, potassium, calcium and magnesium.

* * * * *